(12) United States Patent
Hu et al.

(10) Patent No.: US 11,395,641 B2
(45) Date of Patent: Jul. 26, 2022

(54) ULTRASONIC IMAGING DEVICE AND IMAGING METHOD THEREOF

(71) Applicant: INDUSTRIAL TECHNOLOGY RESEARCH INSTITUTE, Hsinchu (TW)

(72) Inventors: Chang-Lin Hu, Kaohsiung (TW); Chien-Ju Li, Zhubei (TW); Guo-Zua Wu, Taichung (TW); Chih-Chi Chang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 306 days.

(21) Appl. No.: 16/230,168

(22) Filed: Dec. 21, 2018

(65) Prior Publication Data
US 2020/0196990 A1    Jun. 25, 2020

(51) Int. Cl.
*A61B 8/00*    (2006.01)
*A61B 8/08*    (2006.01)
(Continued)

(52) U.S. Cl.
CPC .............. *A61B 8/5207* (2013.01); *A61B 8/14* (2013.01); *A61B 8/42* (2013.01); *A61B 8/5215* (2013.01);
(Continued)

(58) Field of Classification Search
CPC ....... A61B 8/5215; A61B 8/14; A61B 8/4488; A61B 8/5207; A61B 8/4427; G01S 7/52047; G01S 7/52096; G01S 15/8927
See application file for complete search history.

(56) References Cited

U.S. PATENT DOCUMENTS

| | | | | |
|---|---|---|---|---|
| 5,655,536 A | * | 8/1997 | Takamizawa | ....... G01S 15/8925 600/447 |
| 5,897,501 A | | 4/1999 | Wildes et al. | |

(Continued)

FOREIGN PATENT DOCUMENTS

| | | |
|---|---|---|
| CN | 101410061 A | 4/2009 |
| CN | 106028952 A | 10/2016 |

(Continued)

OTHER PUBLICATIONS

Bae et al., "A Novel Beamforming Method for Wireless Ultrasound Smart Probe," 2014 IEEE International Ultrasonics Symposium Proceedings, 2014, pp. 2185-2188.
(Continued)

*Primary Examiner* — Christopher Koharski
*Assistant Examiner* — Taylor Deutsch
(74) *Attorney, Agent, or Firm* — Birch, Stewart, Kolasch & Birch, LLP

(57) ABSTRACT

An ultrasonic imaging device includes an ultrasonic generating unit and an ultrasonic imaging processing unit. The ultrasonic generating unit repeatedly turns on N of M ultrasonic array elements of the ultrasonic probe multiple times as a group of array elements for linear scanning, and each scan is to emit an ultrasonic signal by each group of array elements and receive an echo signal of the ultrasonic signal. The ultrasonic imaging processing unit extracts a central echo signal from the echo signal in each scan to form a channel signal, and according to the arrival time of the echo signals, each central echo signal in the channel signal is delayed and summed to generate a modified channel signal. The modified channel signal is subjected to image synthesis process to obtain an ultrasonic image.

14 Claims, 4 Drawing Sheets

(51) Int. Cl.
*A61B 8/14* (2006.01)
*G01S 15/89* (2006.01)
*G01S 7/52* (2006.01)

(52) U.S. Cl.
CPC ......... *G01S 15/8927* (2013.01); *A61B 8/4488* (2013.01); *G01S 7/52096* (2013.01)

(56) References Cited

U.S. PATENT DOCUMENTS

| | | | |
|---|---|---|---|
| 2005/0228279 | A1 | 10/2005 | Ustuner et al. |
| 2009/0016163 | A1* | 1/2009 | Freeman ............ G01S 15/8927 367/103 |
| 2014/0050048 | A1 | 2/2014 | Jensen et al. |
| 2014/0232956 | A1 | 8/2014 | Kwon et al. |
| 2015/0073277 | A1* | 3/2015 | Hayashi ............... G10K 11/346 600/447 |
| 2015/0359512 | A1 | 12/2015 | Boctor et al. |
| 2016/0139252 | A1 | 5/2016 | Katsuyama |
| 2016/0338674 | A1* | 11/2016 | Yamamoto ............... A61B 8/14 |
| 2017/0071579 | A1* | 3/2017 | Ko ...................... A61B 8/4488 |
| 2017/0209121 | A1* | 7/2017 | Davis, Sr. ............ A61B 8/4494 |
| 2018/0021012 | A1* | 1/2018 | Hiroshima ........... A61B 8/4488 600/459 |
| 2018/0206824 | A1* | 7/2018 | Taniguchi ........... G01S 15/8963 |

FOREIGN PATENT DOCUMENTS

| | | |
|---|---|---|
| TW | 201325556 A | 7/2013 |
| TW | I435710 B | 5/2014 |

OTHER PUBLICATIONS

Bae et al., "A Study of Synthetic-Aperture Imaging with Virtual Source Elements in B-Mode Ultrasound Imaging Systems," IEEE Transactions on Ultrasonics, Ferroelectrics, and Frequency Control, vol. 47, No. 6, Nov. 2000, pp. 1510-1519.

Frazier et al., "Synthetic Aperture Techniques with a Virtual Source Element," IEEE Transactions on Ultrasonics, Ferroelectrics, and Frequency Control, vol. 45, No. 1, Jan. 1998, pp. 196-207.

Hasegawa et al., "Effect of Element Directivity on Adaptive Beamforming Applied to High-Frame-Rate Ultrasound," IEEE Transactions on Ultrasonics, Ferroelectrics, and Frequency Control, vol. 62, No. 3, Mar. 2015, pp. 511-523.

Hemmsen et al., "Implementation of synthetic aperture imaging on a hand-held device," 2014 IEEE International Ultrasonics Symposium Proceedings, 2014, pp. 2177-2180.

Hemmsen et al., "Synthetic Aperture Sequential Beamformation applied to medical imaging," EUSAR 2012, pp. 34-37.

Ianni et al., "A Vector Flow Imaging Method for Portable Ultrasound Using Synthetic Aperture Sequential Beamforming," IEEE Transactions on Ultrasonics, Ferroelectrics, and Frequency Control, vol. 64, No. 11, Nov. 2017, pp. 1655-1665.

Ianni et al., "System-Level Design of an Integrated Receiver Front End for a Wireless Ultrasound Probe," IEEE Transactions on Ultrasonics, Ferroelectrics, and Frequency Control, vol. 63, No. 11, Nov. 2016, pp. 1935-1946.

Jensen et al., "Implementation of Synthetic Aperture Imaging in Medical Ultra-Sound: The Dual Stage Beamformer Approach," EUSAR 2010, 2010, pp. 434-437.

Kortbek et al., "Sequential beamforming for synthetic aperture imaging," Ultrasonics, vol. 53, 2013, pp. 1-16.

Mozumi et al., "Adaptive Beamformer Combined with Phase CoherenceWeighting Applied to Ultrafast Ultrasound," Applied Sciences, vol. 8, No. 204, 2018, pp. 1-13.

O'Donnell, "Efficient Parallel Receive Beam Forming for Phased Array Imaging Using Phase Rotation," 1990 Ultrasonics Symposium, 1990, pp. 1495-1498.

Synnevåg et al., "Adaptive Beamforming Applied to Medical Ultrasound Imaging," IEEE Transactions on Ultrasonics, Ferroelectrics, and Frequency Control, vol. 54, No. 8, Aug. 2007, pp. 1606-1613.

Taiwanese Office Action and Search Report for Taiwanese Application No. 107146541, dated Dec. 11, 2019.

* cited by examiner

ULTRASONIC IMAGING DEVICE AND IMAGING METHOD THEREOF

TECHNICAL FIELD

The disclosure relates in general to an imaging device and an imaging method thereof, and more particularly to an ultrasonic imaging device and an imaging method thereof.

BACKGROUND

In the technology of ultrasonic image synthesis, there are two key factors that affect image quality, one is the delay error caused by phase aberration during focus imaging, and the other is the size of ultrasonic aperture. The delay error increases the beam side lobes of the ultrasound imaging, and thereby causes degradation of focusing and quality of the ultrasonic image. The size of the ultrasonic aperture, that is, the number of array elements of the ultrasonic probe, affects the resolution of the ultrasonic image, and the more the number of array elements, the higher the cost and the larger the amount of calculation.

However, in medical ultrasound field, in order to provide correct clinical diagnosis and analysis, there must be better image quality, such that the hardware of ultrasonic imaging device cannot be further simplified. If the medical ultrasonic imaging device is simplified into a power-saving and portable ultrasonic imaging device, the number of array elements is reduced, the calculation amount of hardware is reduced, and the image quality of ultrasonic imaging device is affected, thereby improvement of image resolution and simplification of hardware device often require trade-off.

SUMMARY

The disclosure is directed to an ultrasonic imaging device and an imaging method thereof, which can effectively reduce energy loss and hardware burden during ultrasonic emission by reducing the emitting source of focused ultrasound, thereby achieving the effects of power saving, portable and high resolution image.

According to one embodiment, an ultrasonic imaging device is provided, which includes an ultrasonic generating unit and an ultrasonic imaging processing unit. The ultrasonic generating unit includes an ultrasonic probe, a transmitting unit and a receiving unit. The ultrasonic probe is connected to the transmitting unit and the receiving unit, and the ultrasonic probe includes M ultrasonic array elements, and the ultrasonic generating unit repeatedly multiple times and selectively turns on N ultrasonic array elements of the ultrasonic probe as a group of array elements for scanning, each scan is to emit an ultrasonic signal by the group of array elements and receive an echo signal of the ultrasonic signal, where M is greater than N, M and N are positive integers greater than one. The ultrasonic imaging processing unit extracts a central echo signal from the echo signal in each scan to form a channel signal. According to an arrival time of each echo signal, each central echo signal in the channel signal is delayed and summed to generate a modified channel signal, and the modified channel signal is subjected to image synthesis process to obtain an ultrasonic image.

According to another embodiment, an ultrasonic imaging method is provided, comprising the following steps. The N ultrasonic array elements of the ultrasonic probe are selectively turned on multiple times as a group of array elements for scanning, and each time an ultrasonic signal is transmitted by the array element and an echo signal of the ultrasonic signal is received. A central echo signal is extracted from the echo signal in each scan to form a channel signal. The arrival time of each central echo signal is calculated to delay and sum each of the central echo signals in the channel signal to generate a modified channel signal. The modified channel signal is subjected to image synthesis process to obtain an ultrasonic image.

The above and other aspects of the disclosure will become better understood with regard to the following detailed description of the preferred but non-limiting embodiment(s). The following description is made with reference to the accompanying drawings.

DETAILED DESCRIPTION

Detailed descriptions of the disclosure are disclosed below with a number of embodiments. However, the disclosed embodiments are for explanatory and exemplary purposes only, not for limiting the scope of protection of the disclosure. Similar/identical designations are used to indicate similar/identical elements. Directional terms such as above, under, left, right, front or back are used in the following embodiments to indicate the directions of the accompanying drawings, not for limiting the disclosure.

Figure 1:
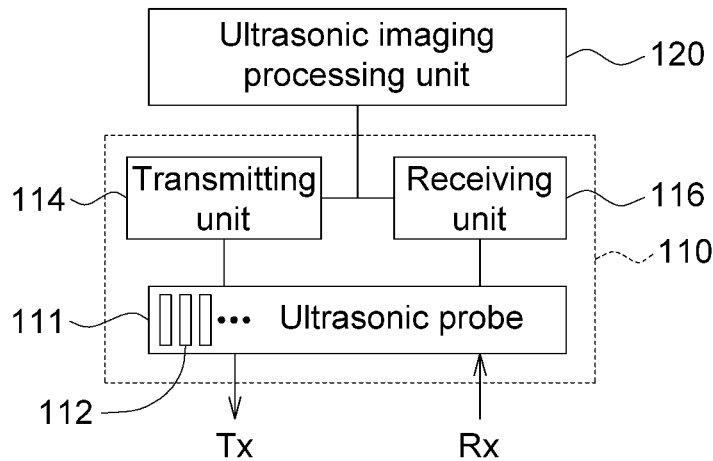
FIG. 1 is a schematic diagram of an ultrasonic imaging device according to an embodiment of the disclosure.

According to an embodiment of the disclosure, an ultrasonic imaging device is provided. As shown in FIG. 1, the ultrasonic imaging device 100 includes an ultrasonic generating unit 110 and an ultrasonic imaging processing unit 120. The ultrasonic generating unit 110 includes, for example, an ultrasonic probe 111, a transmitting unit 114, a receiving unit 116, a processor (not shown) and the like. The ultrasonic probe 111 is, for example, a probe of linear array, a probe of phased array, or other types of probes. The ultrasonic probe 111 includes a plurality of ultrasonic array elements 112, and each of the ultrasonic array elements 112 is a transducer for converting the pulse voltage signal outputted by the high voltage pulse channel in the transmitting unit 114 into a mechanically oscillated ultrasound and the ultrasound is sent to the inside of the organism. In addition, the processor controls the transmission time of the pulse voltage signal of each channel to generate an ultrasonic signal Tx of different transmission time.

In addition, the ultrasonic array element 112 can receive the echo signal Rx of the ultrasound reflected by the scatter inside the organism, and the echo signal Rx is converted into a pulse voltage signal to obtain a channel signal from the receiving unit 116. When the wavelength of the incident ultrasound is much larger than the diameter of the scatter inside the organism, the scattering phenomenon of the ultrasound occurs, and the reverse scatter signal will appear bright speckles randomly in the ultrasonic image. This is the so-called "speckle noise". The presence of speckle noise and side lobe blurs the fine-grained image and reduces the contrast and resolution of the ultrasonic image.

In order to reduce the calculation amount of hardware, in the present embodiment, the ultrasonic generating unit 110 first adjusts the size of the ultrasonic aperture according to the position of the target object, that is, adjusts the respective number and position of the ultrasonic array elements 112 turning on and off in the ultrasonic probe to reduce the number of ultrasonic sources. After that, the ultrasonic imaging processing unit 120 extracts an echo signal from the echo signals Rx of each group for beamforming, and reconstructs an ultrasound image by using a set of channel signals after beamforming.

Since the ultrasonic generating unit 110 of the embodiment does not need to turn on all the array elements 112 of the ultrasonic probe, the ultrasonic emission energy can be reduced, and the effect of power saving can be achieved. In addition, the ultrasonic imaging processing unit 120 of the present embodiment can perform image processing with a lower amount of data (only the central echo signal is extracted at one time), thereby avoiding a complicated operation process, and reducing the calculation amount of the hardware. Therefore, the present embodiment can be applied to portable ultrasound imaging devices.

Referring to FIG. 1, according to an embodiment of the disclosure, the ultrasonic imaging device 100 includes an ultrasonic generating unit 110 and an ultrasonic imaging processing unit 120. The ultrasonic generating unit 110 includes an ultrasonic probe 111, a transmitting unit 114, and a receiving unit 116. The ultrasonic probe 111 is connected to the transmitting unit 114 and the receiving unit 116 and includes M ultrasonic array elements 112. The ultrasonic generating unit 110 repeatedly multiple times and selectively turns on N ultrasonic array elements 112 of the ultrasonic probe 111 as a group of array elements for scanning, each scan is to emit an ultrasonic signal Tx by the array group and receive an echo signal Rx of the ultrasonic signal Tx, where M is greater than N, and M and N are positive integers greater than one. In an embodiment, M is 128 as an example, and N is 3 to 5 for example, but the number of M and N is not limited.

That is to say, the ultrasonic generating unit 110 selects one group of 3 to 5 ultrasonic array elements 112 at different positions from 128 array elements at each time, so that an ultrasonic signal Tx can be transmitted from the selected array elements and the echo signal Rx is received to detect the position of the imaging point for scanning. When the number of N increases, the brightness of the echo signal Rx can be relatively high. However, when the number of N is too large, the echo signal Rx is too complicated, difficult to focus and excessive noises are generated, it may cause degradation of image resolution.

Figure 2:
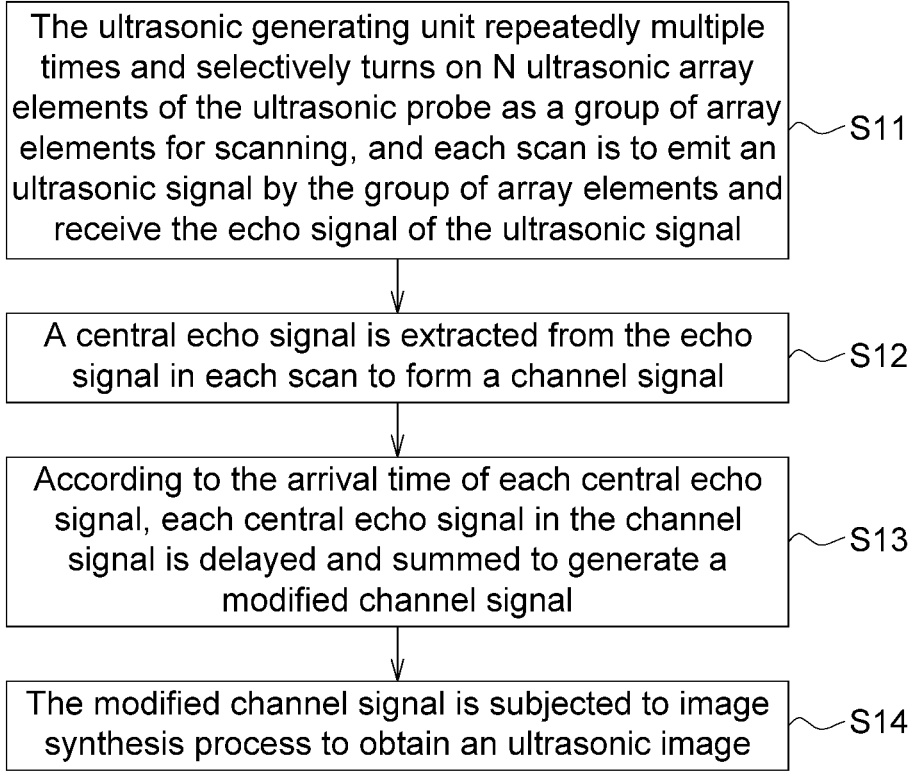
FIG. 2 is a schematic flow chart of an ultrasonic imaging method according to an embodiment of the disclosure.

The ultrasonic imaging processing unit 120 is configured to process the received echo signals Rx of the plurality of ultrasonic signals Tx. Referring to FIG. 1 and FIG. 2 together, FIG. 2 is a schematic flow chart of the ultrasonic imaging method according to an embodiment of the disclosure, which includes the following steps S11-S14. In step S11, the ultrasonic generating unit 110 repeatedly multiple times and selectively turns on the N ultrasonic array elements 112 of the ultrasonic probe 111 as a group of array elements Ai for scanning, and each scan is to emit an ultrasonic signal Tx by the group of array elements and receive the echo signal Rx of the ultrasonic signal Tx. In step S12, a central echo signal Rc is extracted from the echo signals Rx in each scan to form a channel signal. In step S13, according to the arrival time of each central echo signal Rc, each central echo signal Rc of the channel signal is delayed and summed to generate a modified channel signal. In step S14, the modified channel signal is subjected to image synthesis process to obtain an ultrasonic image.

Figure 3A:
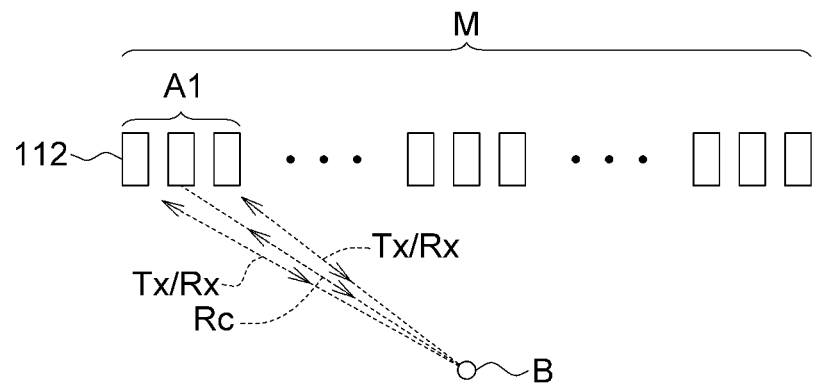
FIGS. 3A to 3D are diagrams respectively showing the operation of the ultrasonic generating unit according to an embodiment of the disclosure.

Referring to FIG. 3A, in an embodiment, the ultrasonic probe 111 of the ultrasonic generating unit 110 includes M ultrasonic array elements 112. During a single scan, the N ultrasonic array elements 112 connected to the transmitting unit 114 are selectively turned on from the M ultrasonic array elements 112, and the selected N ultrasonic array elements 112 can form a group of array elements Ai, and the remaining unselected M-N ultrasonic array elements 112 are turned off. In the single group of array elements Ai, the transmission time of each of the ultrasonic array elements 112 may be the same or different, and when each of the ultrasonic element elements has the same transmission time, a plane wave may be generated; when each of the ultrasonic array elements 112 has different transmission times, an ultrasound having a focusing effect can be generated, so that the ultrasonic signals Tx having different effects can be generated by the same or different transmission times. In addition, when a group of array elements Ai generates the ultrasonic signal Tx, the echo signal Rx of the ultrasonic signal Tx can be correspondingly received by the same group of array elements Ai (i.e., N ultrasonic array elements 112). In another embodiment, when the ultrasonic signal Tx is generated by a group of array elements Ai, the echo signal Rx of the ultrasonic signal Tx is received only by the central portion of the ultrasonic array elements 112 of the same group of array elements Ai (i.e., N ultrasonic array elements 112), but the embodiment is not limited thereto.

Next, referring to FIGS. 3A to 3D, taking each group of array elements Ai containing three ultrasonic array elements 112 (i.e., N=3) as an example, when a first scan is performed, the leftmost three ultrasonic array elements 112 from the M ultrasonic array elements 112 are selectively turned on as the first group of array elements A1, and the first set of ultrasonic signals Tx are transmitted. When the ultrasonic signals Tx are transmitted to the object B and scattered, echo signals Rx are generated and received by the first group of array elements A1. Then, during the second scan, the selected three ultrasonic array elements 112 can be shifted to the right from the first group of array elements A1 by one ultrasonic array element 112, that is, during the second scan, the second to fourth ultrasonic array elements 112 on the leftmost side of the M ultrasonic arrays elements 112 are selectively turned on as the second group of array elements A2, and when the second group of array elements A2 generates the second set of ultrasonic signals Tx, the second group of array elements A2 correspondingly receives the echo signals Rx of the second set of ultrasonic signals Tx; during the i-th scan, the i-th set of ultrasonic signals Tx are generated by the i-th group of array elements Ai, and the echo signals Rx of the i-th set of ultrasonic signals Tx can be correspondingly received by the i-th group of array elements Ai, where i=1–P, P may be a positive integer smaller than M. Therefore, after P times of transmission and reception, a total of P set of the echo signals Rx of the ultrasonic signals Tx can be obtained.

Figure 3B:
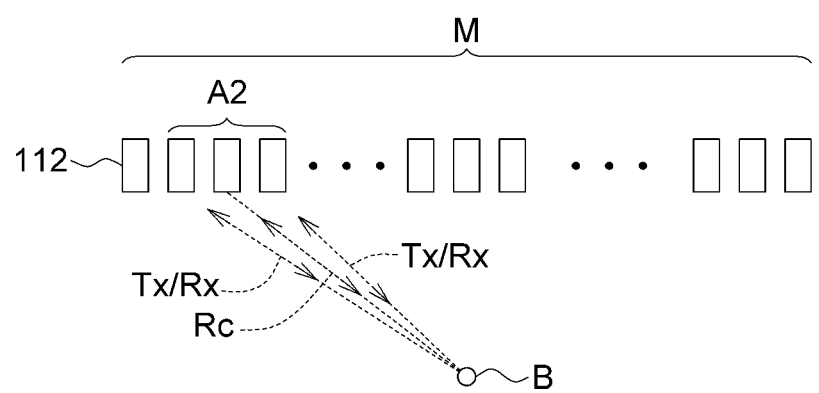
Figure 3C:
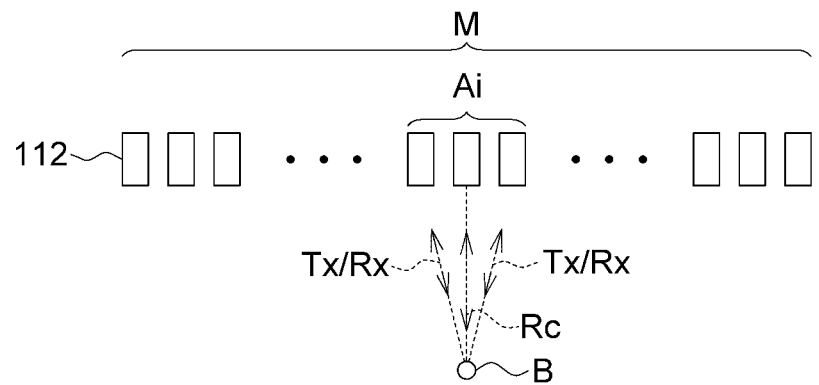
Figure 3D:
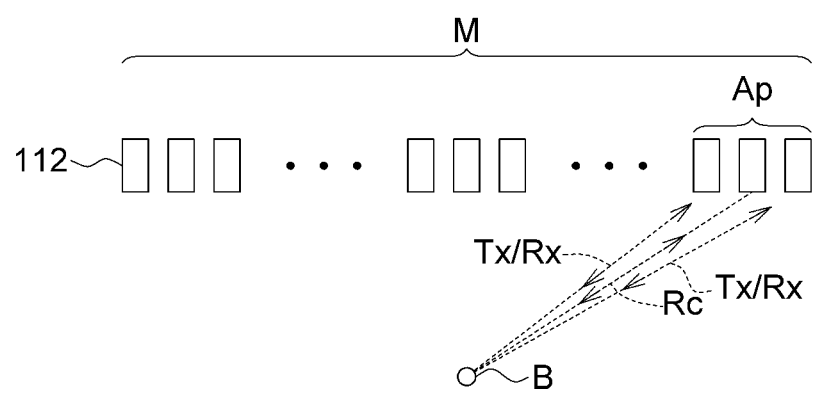

In the present embodiment, after each set of ultrasonic signals Tx is transmitted (i.e., each scan), the ultrasonic array elements 112 can be shifted by at least one ultrasonic array element 112 to be the next group of array elements Ai until all M array elements 112 are completely transmitted. It is to be noted that the number of ultrasonic array elements 112 that are shifted to scan per each time can be adjusted as needed, and is not limited to those enumerated. As shown in FIGS. 3A to 3B, the positions of the two groups of array elements A1 and A2 that sequentially emit the ultrasonic signals Tx are, for example, separated by the width of one ultrasonic array element 112. In another embodiment, the positions of the two groups of array elements A1 and A2 that sequentially emit the ultrasonic signals Tx are, for example, separated by the width of two or more ultrasonic array elements 112.

When the i-th group of array elements Ai receives the echo signals Rx of the i-th set of ultrasonic signals Tx, the ultrasonic imaging processing unit 120 extracts a central echo signal Rc from the echo signals Rx of the i-th set of ultrasonic signals Tx. For example, when N is an odd number (such as 3 or 5), the central echo signal Rc is an echo signal Rx received from the ultrasonic array element 112 in the center of the group of array elements Ai, that is, the central echo signal Rc is an echo signal Rx received by the (1+N)/2th ultrasonic array element 112 in the group of array elements Ai. When N is an even number (such as 4), the central echo signal Rc is the average of the echo signals Rx received from the two ultrasonic array elements 112 in the center of the group of array elements Ai, that is, the central echo signal Rc is the average of the echo signals Rx received by 1+(N−1)/2th and 1+(N+1)/2th array elements 112 in the group of array elements Ai. In an embodiment, the ultrasonic generating unit 110 can transmit the transmitting ultrasonic signals Tx and receive the corresponding echo signals Rx by the same group of array elements Ai at a time, and then extract the central echo signal Rc by the ultrasonic imaging processing unit 120. In another embodiment, in each scan, the ultrasonic generating unit 110 transmits the ultrasonic signals Tx from a group of array elements Ai, but only receives the echo signals Rx by the ultrasonic array elements 112 in the center of the same group of array elements Ai. When N is an odd number, the central echo signal Rc is the echo signal Rx received by the intermediate (i.e., (1+N)/2th) ultrasonic array element 112; and when N is an even number, the echo signals Rx received by the intermediate (i.e., 1+(N−1)/2th and 1+(N+1)/2th) ultrasonic array elements 112 are averaged first in the ultrasonic imaging processing unit 120 and thus can be used as the central echo signal Rc. The ultrasonic imaging processing unit 120 can form a channel signal by the central echo signals Rc extracted in each scan, wherein the number of central echo signals Rc in the channel signal can be P.

Figure 4:
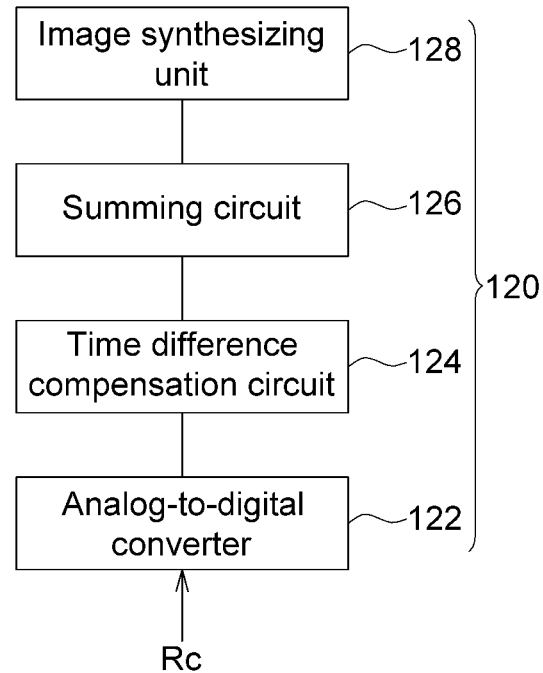
FIG. 4 is a schematic diagram showing the ultrasonic imaging processing unit.

Referring to FIG. 4, in an embodiment, the ultrasonic imaging processing unit 120 includes an analog-to-digital converter 122, a time difference compensation circuit 124, a summing circuit 126, and an image synthesizing unit 128. The ultrasonic imaging processing unit 120 captures the central echo signals Rc of each scan to form a channel signal. Since the channel signal is an analog signal, the ultrasonic imaging processing unit 120 can convert the channel signal into a digital channel signal by the analog-to-digital converter 122. In addition, there is a problem that the number of samples is insufficient (P<M) when the channel signal is converted into a digital channel signal. Therefore, the number of samples obtained from the ultrasonic array elements 112 can be increased by using an interpolation method to make the number of the digital channel signal reaches M. The time difference compensation circuit 124 is configured to receive the converted digital channel signal, and obtain a compensation value for each central echo signal Rc according to the arrival times $\tau_1$ to $\tau_M$ and the time difference of each central echo signal Rc. The summing circuit 126 delays and sums each central echo signal Rc in the channel signal according to the compensation value to obtain a modified channel signal after delay and sum. Then, the image synthesizing unit 128 performs beamforming according to the modified channel signal and performs an image synthesis process to obtain an ultrasonic image.

Figure 5:
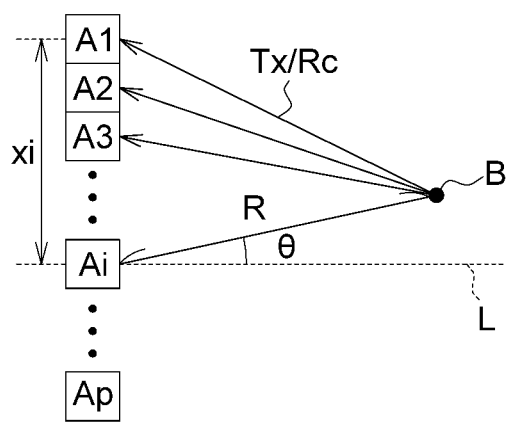
FIG. 5 is a schematic diagram showing the delay time of each central echo signal.

The method of how does the ultrasonic array probe synthesize a specific point in the space, use the distance derived from the transmitted and received signals to calculate difference of the delay time of each array element, sum a total of the delay times, and then obtain the image of the specific point in the space is illustrated in the above. This way of synthesizing images is called delay and sum. As shown in FIG. 5, in the case of sector scan mode of ultrasound, images at any point in the space can be represented by polar coordinates (R, θ). It is assumed that Si is the central echo signal Rc received by the i-th group of array elements Ai, and O(t) is the delayed and summed image.

$$O(t) = \sum_{i=1}^{M} S_i(t - \tau(x_i, R, \theta))$$

τ(xi, R, θ) is the time when the central echo signal Rc reaches the group of array elements Ai from the object B after the scattering of the ultrasonic signal Tx by the object B, that is $\tau_1$-$\tau_M$, and xi is the vertical distance from the central ultrasonic array element 112 of the group of array elements Ai to the center line L, R is the distance from the object point B to the ultrasonic array element 112 passing through the center line L, and θ is the angle between the line segment R and the center line L, which is calculated as follows, and c is the speed of light:

$$\tau(x_i, R, \theta) = \frac{((x_i - R\sin\theta)^2 + R^2\cos^2\theta)^{1/2}}{c} = \frac{R}{c}\left(1 + \frac{x_i^2}{R^2} - \frac{2x_i}{R}\sin\theta\right)^{1/2}$$

In the Fresnel field, τ(xi, R, θ) can be simplified as follows:

$$\tau(x_i, R, \theta) \approx \frac{R}{c}\left(1 + \frac{x_i^2}{2R^2} - \frac{x_i}{R}\sin\theta - \frac{x_i^2}{2R^2}\sin^2\theta\right) =$$
$$\frac{R}{c}\left(1 - \frac{x_i}{R}\sin\theta - \frac{x_i^2}{2R^2}\cos^2\theta\right) = \frac{R}{c} - \frac{x_i\sin\theta}{c} + \frac{x_i^2\cos^2\theta}{2Rc}$$

In the present embodiment, since the central echo signal Rc is taken as the channel signal in each scan, the central ultrasonic array element 112 of each group of array elements Ai can be regarded to have the same back and forth paths when the current ultrasonic signal Tx transmits to the object B and returns to the central ultrasonic array element 112 by the central echo signal Rc. The transmission time of the ultrasonic signal Tx is the same as the receiving time of the echo signal Rc, both are τ(xi, R, θ), so that a delay time of the central ultrasonic array element 112 of the i-th group of array elements Ai receiving the central echo signal Rc is two times of τ(xi, R, θ), which is expressed as follows:

$$\tau^R(x_i, R, \theta) = 2 \times \left(\frac{R}{c} - \frac{x_i\sin\theta}{c} + \frac{x_i^2\cos^2\theta}{2Rc}\right)$$

According to the above result of calculation, the time difference compensation circuit 124 can obtain the delay time of each central echo signal Rc in the channel signal for the summing circuit 126 to perform delay and sum.

In the ultrasonic imaging device and the imaging method thereof disclosed in the above embodiments, an ultrasonic probe is used to transmit an ultrasonic signal in linear scan and receive an echo signal of the ultrasonic signal, and then the central echo signal is extracted from each echo signal as a channel signal. Then, the time domain signal processing method of the improved delay and sum is used to improve the image quality of the ultrasonic imaging. The present disclosure performs ultrasonic imaging in the above embodiment, which can reduce the ultrasonic emission energy, achieve power saving and portability, reduce the calculation amount of hardware, reduce cost and improve safety, and the present disclosure can also use the image weighting technology that can effectively reduce speckle noise and improve lateral resolution.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An ultrasonic imaging device, comprising:
   an ultrasonic generating unit comprising an ultrasonic probe, a transmitting unit and a receiving unit, the ultrasonic probe being connected to the transmitting unit and the receiving unit, the ultrasonic probe comprising M ultrasonic array elements, the ultrasonic generating unit selectively turns on N ultrasonic array elements of the ultrasonic probe as a group of array elements, and repeatedly multiple times for creating a plurality of scans, and each scan of the plurality of scans is to emit an ultrasonic signal by the group of array elements and receive an echo signal of the ultrasonic signal, where M is greater than N, and M, N are positive integers greater than one; and
   an ultrasonic imaging processing unit only extracts a central echo signal from the echo signal in each scan of the plurality of scans to form a channel signal, and according to an arrival time of the echo signal, each central echo signal of the N ultrasonic array elements in the channel signal is delayed and summed and no other echo signal of the ultrasonic signal of the N−1 ultrasonic array elements is delayed and summed to generate a modified channel signal, and the modified channel signal is subjected to image synthesis process to obtain an ultrasonic image.

2. The ultrasonic imaging device according to claim 1, wherein when the N is an odd number, the central echo signal is received by the ultrasonic element in the center of the group of array elements.

3. The ultrasonic imaging device according to claim 1, wherein when the N is an even number, the central echo signal is an average of the echo signals received from two of the ultrasonic array elements in the center of the group of array elements.

4. The ultrasonic imaging device according to claim 1, wherein after each scan of the plurality of scans of the ultrasonic signal is transmitted, the ultrasonic array elements is shifted to scan by at least one ultrasonic array element to be a next group of array elements.

5. The ultrasonic imaging device according to claim 1, wherein N is 3 to 5.

6. The ultrasonic imaging device according to claim 1, wherein the ultrasonic imaging processing unit comprises an analog-to-digital converter, a time difference compensation circuit, a summing circuit, and an image synthesizing unit, wherein the analog-to-digital converter converts the channel signal into a digital channel signal, the time difference compensation circuit receives the digital channel signal, and obtains a compensation value for the central echo signal according to the arrival time and a time difference of each of the central echo signals, the summing circuit delays and sums the central echo signals in the digital channel signal according to the compensation values to generate the modified channel signal, and the image synthesizing unit performs image synthesis process according to the modified channel signal to get the ultrasound image.

7. The ultrasonic imaging device according to claim 1, wherein a delay time of each group of array elements receiving the central echo signal is two times of a time of each of the central echo signals arriving from an object to each group of array elements.

8. A method of ultrasonic imaging, comprising:
   selectively turning on N ultrasonic array elements in an ultrasonic probe as a group of array elements and repeatedly multiple times for creating a plurality of scans, and each scan of the plurality of scans is to emit an ultrasonic signal by each group of array elements and receive an echo signal of the ultrasonic signal;
   only extracting a central echo signal from the echo signal in each scan of the plurality of scans to form a channel signal;
   delaying and summing each of the central echo signals of the N ultrasonic array elements in the channel signal according to an arrival time of each central echo signal to generate a modified channel signal, and no other echo signal of the ultrasonic signal of the N−1 ultrasonic array elements is delayed and summed; and
   the modified channel signal is subjected to image synthesis process to obtain an ultrasonic image.

9. The ultrasonic imaging method according to claim 8, wherein when the N is an odd number, the central echo signal is received by the ultrasonic element in the center of the group of array elements.

10. The ultrasonic imaging method according to claim 8, wherein the N is an even number, the central echo signal is an average of the echo signals received from two of the ultrasonic array elements in the center of the group of array elements.

11. The ultrasonic imaging method according to claim 8, wherein after each scan of the plurality of scans of the ultrasonic signal is transmitted, the ultrasonic array elements is shifted to scan by at least one ultrasonic array element to be a next group of array elements.

12. The ultrasonic imaging method according to claim 8, wherein N is 3 to 5.

13. The ultrasonic imaging method according to claim 8, wherein a compensation value of each of the central echo signals is obtained according to the arrival time and a time difference of each of the central echo signals, and each of the echo signals is delayed and summed according to the compensation values.

14. The ultrasonic imaging method according to claim 8, wherein a delay time of each group of array elements receiving the central echo signal is two times of a time of each of the central echo signals arriving from an object to each group of array elements.

* * * * *